United States Patent
Kuwabara

(10) Patent No.: US 8,731,141 B2
(45) Date of Patent: *May 20, 2014

(54) RADIOGRAPHIC IMAGE ACQUIRING APPARATUS, RADIOGRAPHIC IMAGE CAPTURING SYSTEM, AND RADIOGRAPHIC IMAGE CAPTURING METHOD

(75) Inventor: Takeshi Kuwabara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 601 days.

This patent is subject to a terminal disclaimer.

(21) Appl. No.: 13/017,605

(22) Filed: Jan. 31, 2011

(65) Prior Publication Data

US 2011/0211672 A1    Sep. 1, 2011

(30) Foreign Application Priority Data

Mar. 1, 2010 (JP) .................................. 2010-044340

(51) Int. Cl.
  *H05G 1/64* (2006.01)
  *H05G 1/60* (2006.01)
  *H05G 1/56* (2006.01)
  *G06K 9/28* (2006.01)
  *G06K 9/60* (2006.01)

(52) U.S. Cl.
  USPC ............................ 378/116; 378/98.8; 382/132

(58) Field of Classification Search
  USPC ............. 378/4–20, 38–40, 91, 98, 98.5, 98.8, 378/114–116, 162, 165, 189–192, 204, 207, 378/210, 901; 382/128, 131, 132, 318
  See application file for complete search history.

(56) References Cited

U.S. PATENT DOCUMENTS

| | | | |
|---|---|---|---|
| 7,642,537 B2 | 1/2010 | Maack | |
| 7,864,917 B2 | 1/2011 | Ribbing et al. | |
| 2004/0071263 A1 | 4/2004 | Motoki | |
| 2005/0147201 A1 | 7/2005 | Hoffman | |
| 2008/0317214 A1* | 12/2008 | Maack | 378/162 |

FOREIGN PATENT DOCUMENTS

| | | |
|---|---|---|
| CN | 1636514 A | 7/2005 |
| CN | 101156108 A | 4/2008 |

(Continued)

OTHER PUBLICATIONS

Communication pursuant to Article 94(3) EPC, dated Oct. 26, 2012, issued in corresponding EP Application No. 11152562.2, 4 pages.

(Continued)

*Primary Examiner* — Anastasia Midkiff
(74) *Attorney, Agent, or Firm* — Sughrue Mion, PLLC

(57) ABSTRACT

In a radiographic image acquiring apparatus, in the event that one radiation detection device is selected from among a plurality of radiation detection devices, each of which are capable of converting radiation into a radiographic image, the radiographic image acquiring apparatus includes an acquisition unit for acquiring all of the radiographic images from the plurality of radiation detection devices, including the radiographic image from the one radiation detection device, at a time when application of radiation with respect to a subject is carried out.

11 Claims, 6 Drawing Sheets

(56) References Cited

FOREIGN PATENT DOCUMENTS

| CN | 101379392 A | 3/2009 |
|---|---|---|
| EP | 1 867 282 A1 | 12/2007 |
| JP | 04-364834 A | 12/1992 |
| JP | 2004-073462 A | 3/2004 |
| JP | 2007082650 A | 4/2007 |
| JP | 2008132216 A | 6/2008 |
| JP | 2009018208 A | 1/2009 |
| JP | 2009-028373 A | 2/2009 |
| JP | 2009-219586 A | 10/2009 |

OTHER PUBLICATIONS

Communication, dated May 23, 2011, issued in corresponding EP Application No. 11152562.2, 7 pages.
Rejection of the Application, dated Jul. 30, 2013, issued in related JP Application No. 2010-044339, 7 pages in English and Japanese.
Notification of First Office Action, dated Jan. 28, 2014, issued in corresponding CN Application No. 201110037610.5, 13 pages in English and Chinese.

* cited by examiner

RADIOGRAPHIC IMAGE ACQUIRING APPARATUS, RADIOGRAPHIC IMAGE CAPTURING SYSTEM, AND RADIOGRAPHIC IMAGE CAPTURING METHOD

CROSS-REFERENCE TO RELATED APPLICATION

This application is based upon and claims the benefit of priority from Japanese Patent Application No. 2010-044340 filed on Mar. 1, 2010, of which the contents are incorporated herein by reference.

BACKGROUND OF THE INVENTION

1. Field of the Invention

The present invention relates to a radiographic image capturing system and a radiographic image capturing method for irradiating a subject with radiation and converting radiation that has passed through the subject into a radiographic image by means of a radiation detection device. The present invention also relates to a radiographic image acquiring apparatus for acquiring the radiographic image from the radiation detection device.

2. Description of the Related Art

In the medical field, it has widely been practiced to apply radiation to a subject and to convert radiation that has passed through the subject into a radiographic image by a radiation conversion panel, and then to acquire the radiographic image from the radiation conversion panel. One known type of radiation conversion panel is a stimulable phosphor panel, which stores radiation energy representative of a radiographic image in a phosphor, and then, when the stimulable phosphor panel is irradiated with stimulating light, a radiographic image is obtained as stimulated light representative of the stored radiographic image. In this case, the stimulable phosphor panel is supplied to a radiographic image acquiring apparatus, and by carrying out acquisition processing of the radiographic image, the radiographic image can be obtained as a visible image.

Further, recently, in sites of medical practice such as operating rooms or the like, it is necessary to acquire and display radiographic image information from a radiation conversion panel immediately after capturing a radiographic image, for the purpose of quickly and appropriately treating patients. As a radiation conversion panel which meets such a requirement, there have been developed a direct conversion type of radiation detection device, in which solid state detection elements are used that directly convert radiation into electrical signals, as well as an indirect conversion type of radiation detection device utilizing a scintillator, which converts radiation into visible light, and solid state detection elements for converting the visible light into electrical signals.

Incidentally, in a medical organization, a radiographic image capturing system may be set up having a plurality of radiation detection devices equipped with the aforementioned radiation conversion panels. (See, for example, Japanese Laid-Open Patent Publication No. 2004-073462 and Japanese Laid-Open Patent Publication No. 2009-219586.)

An explanation shall now be made concerning application of radiation to a subject (image capturing) and acquisition processing of radiographic images, for a case in which all of the radiation detection devices within the radiographic image capturing system are radiation detection devices equipped with a radiation conversion panel (hereinafter also referred to as a Flat Panel Detector or FPD) of a direct conversion or indirect conversion type.

First, a doctor or radiological technician selects one radiation detection device from among the plurality of radiation detection devices and, concerning the FPD of the selected radiation detection device, prepares the same so as to be capable of storing electrical signals (electrical charges) converted from the radiation.

Next, the doctor or radiological technician positions the subject (patient) between a radiation source and the one radiation detection device. In such a state, when radiation is irradiated from the radiation source onto the one radiation detection device through the subject, the FPD converts radiation that has passed through the subject into electrical charges, which are then stored. After application of radiation, the radiographic image acquiring apparatus acquires the electrical charges that have been stored in the FPD as a radiographic image corresponding to the subject.

In this manner, with the radiographic image capturing system according to the conventional art, one radiation detection device is selected, radiation is irradiated onto the radiation detection device from the radiation source while passing through the subject, and by acquiring a radiographic image from the one radiation detection device, the radiographic image acquiring apparatus associates the subject with the radiographic image.

Incidentally, responsive to a condition of the one radiation detection device (for example, in the event of malfunctioning of the one radiation detection device, or if the charge amount of a battery thereof is not a sufficient charge amount required to capture an image), cases may occur in which image capturing is carried out using a different radiation detection device in place of the one radiation detection device. In such a case, when radiation is irradiated onto the other radiation detection device from the radiation source while passing through the subject, the subject is reflected in the radiographic image of the other radiation detection device.

However, in a case where the radiation detection device is changed, yet one forgets to notify the radiographic image acquiring apparatus of the details concerning carrying out of image capturing, there is a concern that the radiographic image acquiring apparatus may acquire the radiographic image from the selected one radiation detection device, and thus erroneously associate the subject with the radiographic image therefrom. In this case, because when the radiographic image acquiring apparatus acquires the radiographic image from the one radiation detection device, the subject is not properly reflected in the radiographic image, it is determined that an image capturing failure has occurred, and image capturing must be carried out again with respect to the subject.

Stated otherwise, with the radiographic image capturing system according to the conventional art, in the event that the radiation detection device (the other radiation detection device), which is equipped with the FPD that actually was irradiated with radiation, does not match with the radiation detection device (the one radiation detection device) equipped with the FPD from which the radiographic image is acquired, image capturing is carried out again without acquiring the radiographic image possessed by the other radiation detection device and in which the subject's image is reflected, and thus there is a concern that the subject is unnecessarily exposed to radiation.

SUMMARY OF THE INVENTION

The present invention has the object of resolving the aforementioned difficulties and of providing a radiographic image acquiring apparatus, a radiographic image capturing system and a radiographic image capturing method, in which, by reliably and accurately acquiring a radiographic image in which a subject is reflected, it is possible to prevent unnecessary exposure to radiation with respect to the subject.

In the radiographic image acquiring apparatus according to the present invention, in the event that one radiation detection device is selected from among a plurality of radiation detection devices, each of which is capable of converting radiation into a radiographic image, the radiographic image acquiring apparatus comprises an acquisition unit for acquiring all of the radiographic images from the plurality of radiation detection devices, including the radiographic image from the one radiation detection device, at a time when application of radiation with respect to a subject is carried out.

Further, a radiographic image capturing system according to the present invention is equipped with a plurality of radiographic image capturing apparatus having a radiation source that outputs radiation, and a radiation detection device for converting the radiation into a radiographic image, and a radiographic image acquiring apparatus having an acquisition unit which, in the event that one radiation detection device is selected from among the plurality of radiographic image capturing apparatus, acquires all of the radiographic images from the plurality of radiation detection devices, including the radiographic image from the one radiation detection device, at a time when application of radiation with respect to a subject is carried out.

Furthermore, a radiographic image capturing method according to the present invention includes, in the event that one radiation detection device is selected from among a plurality of radiation detection devices, each of which is capable of converting radiation into a radiographic image, a step of carrying out application of radiation with respect to a subject, and a step of acquiring, by an acquisition unit, all of the radiographic images from the plurality of radiation detection devices, including the radiographic image from the one radiation detection device.

According to the aforementioned inventions, an acquisition unit acquires all of the radiographic images from a plurality of radiation detection devices, including a radiographic image from a selected one of the radiation detection devices.

As a result thereof, even in the case that radiation was applied through the subject to the one radiation detection device, or if another radiation detection device is used and radiation was applied through the subject to the other radiation detection device, since the acquisition unit acquires radiographic images from all of the radiation detection devices, among all of the acquired radiographic images, the subject will necessarily be reflected in one of the radiographic images.

Consequently, according to the present invention, since a radiographic image in which the subject is reflected can be acquired reliably and with certainty, unnecessary exposure to radiation with respect to the subject can be prevented.

The radiographic image acquiring apparatus may further include a determining unit for determining, from among each of the radiographic images acquired by the acquisition unit, a significant radiographic image in which the subject is reflected.

As a result thereof, among all of the radiographic images acquired by the acquisition unit, it is possible to determine which of the radiographic images is the significant radiographic image in which the subject is reflected. The significant radiographic image in which the subject is reflected is defined as a radiographic image in which, for example, in the case that the radiographic image is made up of image data consisting of digital data, an average value or the distributed value of intensity of the image data is equal to or greater than a predetermined threshold.

Further, the radiographic image acquiring apparatus may further comprise an image selector which, in the case that the determining unit determines that the significant radiographic image does not exist, selects from among each of the radiographic images, any one of the radiographic images to be regarded as the significant radiographic image.

In accordance therewith, even if a significant radiographic image cannot be obtained, a situation in which a radiographic image of the subject must be recaptured can be avoided by regarding as the significant radiographic image a radiographic image capable of enabling image reading diagnosis yet wherein, for example, the average value or the distributed value of intensity of the image data is slightly lower than the aforementioned threshold value.

Further, in place of the above-mentioned structure, the image selector may select, from among each of the radiographic images acquired by the acquisition unit, any one of the radiographic images to be regarded as a significant radiographic image in which the subject is reflected.

In this case, although determination of the significant radiographic image is not carried out automatically by the determining unit, the significant radiographic image can be selected by a doctor or radiological technician, or even if a significant radiographic image does not exist, the doctor or radiological technician can select a radiographic image capable of enabling image reading diagnosis.

Further, the radiographic image acquiring apparatus may further include an output device for outputting to the exterior the significant radiographic image.

Consequently, a doctor can carry out image reading diagnosis using the significant radiographic image.

Further, in the event that application of radiation with respect to the subject is carried out in an image capturing room, the radiographic image acquiring apparatus may further include an identification information storage unit, which stores identifying information of the plurality of radiation detection devices that reside in the image capturing room, wherein based on the identifying information stored in the identification information storage unit, the acquisition unit acquires all of the radiographic images from the plurality of radiation detection devices that reside in the image capturing room.

Owing thereto, because acquisition processing of radiographic images is carried out only with respect to the plurality of radiation detection devices that reside in the image capturing room, mistakenly carrying out of acquisition processing with respect to radiation detection devices outside of the image capturing room can securely be prevented, and acquisition of the radiographic images can be performed highly efficiently.

Furthermore, the plurality of radiation detection devices may each comprise, respectively, a radiation conversion panel, which converts radiation into electrical charges and stores the electrical charges, and outputs the stored electrical charges to the exterior as electrical signals, wherein each of the radiation conversion panels is placed in a state enabling storage of electrical charges before radiation is applied with respect to the subject.

Owing thereto, since it is unnecessary to apply radiation, as a trigger for instructing each of the radiation conversion panels to store electrical charges, to each of the radiation detection devices before actual image capturing is performed, the structure for instructing storage of electrical charges can be simplified, and the radiation exposure amount to the subject can be lessened.

According to the present invention, because the acquisition unit acquires all of the radiographic images from a plurality of radiation detection devices, including the radiographic image from the one radiation detection device, a radiographic image in which a subject is reflected can be acquired reliably and accurately, and unnecessary exposure to radiation with respect to the subject can be prevented.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Details of a radiographic image capturing system, which is equipped with a radiographic image acquiring apparatus according to the present invention, shall be explained below with reference to FIGS. 1 through 6, in relation to a radiographic image capturing method implemented thereby.

Figure 1:
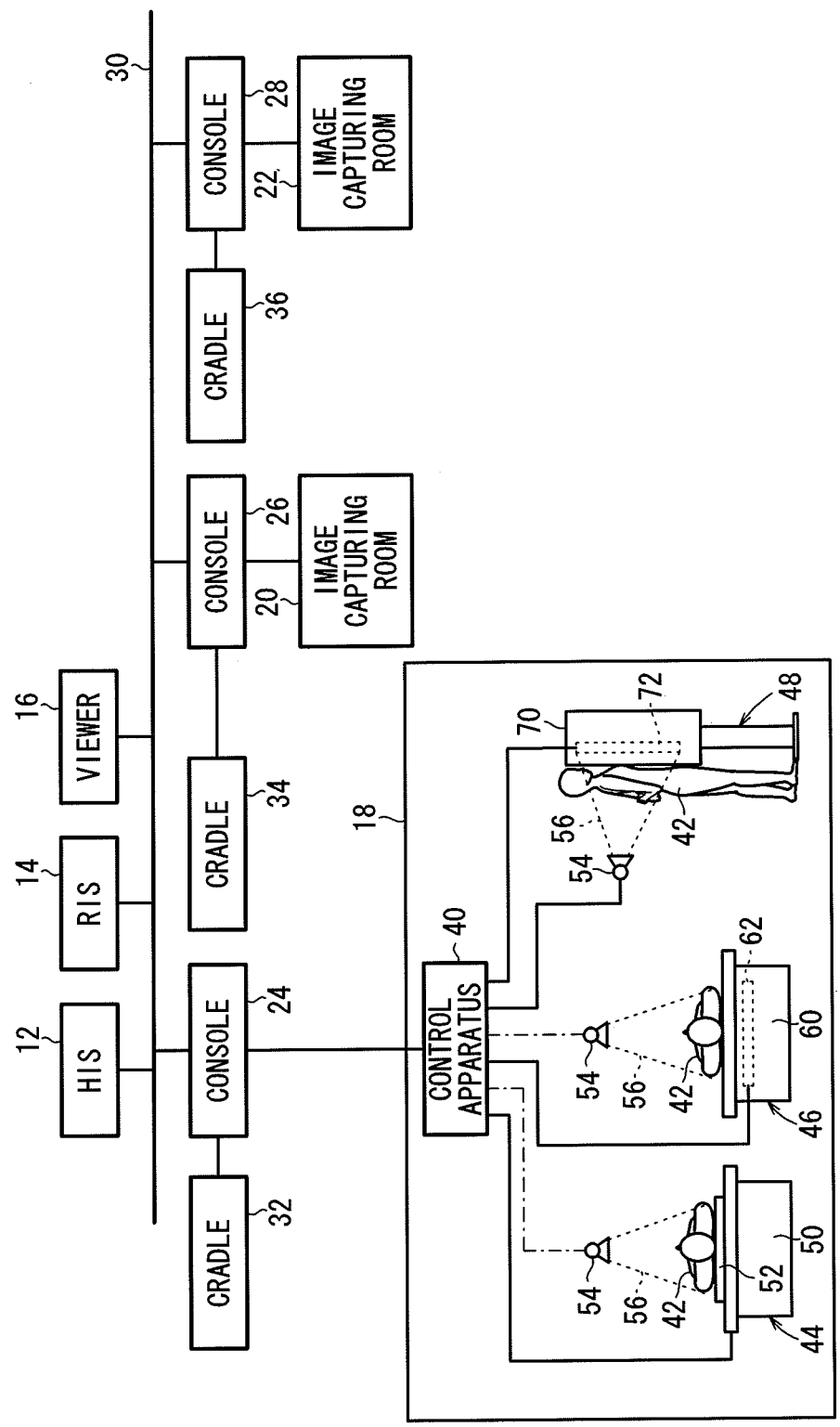
FIG. 1 is a block diagram of a radiographic image capturing system according to an embodiment of the present invention.

As shown in FIG. 1, a radiographic image capturing system 10 according to the present embodiment comprises a hospital information system (HIS) 12 for managing medical information in a hospital, a radiology information system (RIS) 14 for managing processes of capturing radiographic images in the radiological department of the hospital under the management of the HIS 12, a viewer 16 for allowing a doctor to interpret captured radiographic images for the purpose of diagnosis, and consoles 24, 26, 28 installed in respective processing rooms adjacent to a plurality of image capturing rooms 18, 20, 22 for controlling management of respective image capturing apparatus 44, 46, 48 of differing specifications, such components being connected mutually over an in-house network 30. Further, in each of the processing rooms, cradles 32, 34, 36 for enabling charging of radiation detection devices 52, 62, 72 are connected respectively to the consoles 24, 26, 28.

The image capturing room 18 houses therein image capturing apparatus 44, 46 for capturing radiographic images (recumbent image capturing) of a subject 42 while the subject 42 is lying down, an image capturing apparatus 48 for capturing radiographic images (upstanding image capturing) of a subject 42 while the subject 42 is standing, and a control apparatus (acquisition unit) 40 connected between the console 24 and each of the image capturing apparatus 44, 46, 48. A control apparatus 40 and image capturing apparatus 44, 46, 48 are housed similarly in the other image capturing rooms 20, 22. However, such devices have been omitted from illustration in FIG. 1. Further, the radiographic image acquiring apparatus according to the present embodiment is made up collectively from the consoles 24, 26, 28 and the control apparatus 40.

The image capturing apparatus 44 comprises an image capturing base 50 and the radiation detection device 52, which is placed on the image capturing base 50. The image capturing apparatus 46 comprises an image capturing base 60 and the radiation detection device 62, which is disposed in the interior of the image capturing base 60. The image capturing apparatus 48 comprises an upstanding image capturing base 70 and the radiation detection device 72, which is disposed in the interior of the image capturing base 70. Further, in the present embodiment, each of the image capturing apparatus 44, 46, 48 is utilized in common with one radiation source 54. For this purpose, when radiation 56 is applied from the radiation source 54 with respect to the subject 42, in any one of the radiation detection devices, radiation 56 that passes through the subject 42 is converted into a radiographic image, whereas in the other two radiation detection devices, radiographic images are obtained in which the subject 42 is not reflected.

The image capturing apparatus 44 differs from the other two image capturing apparatus 46, 48, in that the radiation detection device 52 is not disposed in the interior of the image capturing base 50. For this reason, the image capturing apparatus is not limited for use in recumbent image capturing as in the example of FIG. 1, and for example, enables image capturing with respect to a predetermined region (e.g., image capturing with respect to a knee region) of the subject 42, in a condition where the subject 42 is seated on the image capturing base 50. Further, in FIG. 1, the control apparatus 40 and each of the image capturing apparatus 44, 46, 48 are interconnected in a wired manner. However, the image capturing apparatus 44, 46, 48 may be interconnected wirelessly. Further, although in FIG. 1, the radiation detection devices 52, 62, 72 are arranged respectively in each of the image capturing apparatus 44, 46, 48, according to the present embodiment, at least two radiation detection devices may be disposed in the image capturing rooms 18, 20, 22. Accordingly, among the three image capturing apparatus 44, 46, 48, concerning the image capturing apparatus in which the radiation detection device is not disposed, the radiation detection device of the other image capturing apparatus may be substituted therein.

Figure 2:
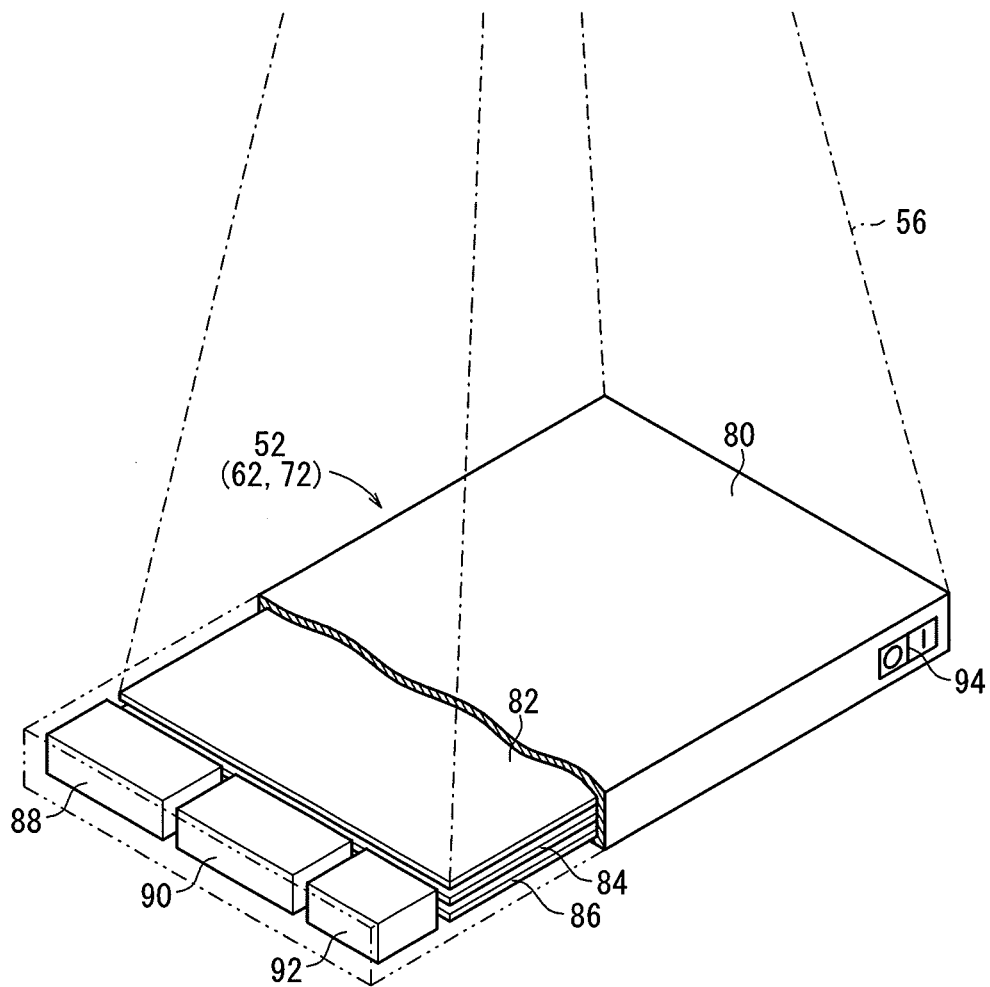
FIG. 2 is an outline schematic view of a radiation detection device.

As shown in FIG. 2, the radiation detection devices 52, 62, 72 that are used in each of the image capturing apparatus 44, 46, 48 include, respectively, casings 80, which are made of a material permeable to radiation 56. The casings 80 house therein a grid 82 for removing scattered rays of the radiation from the subject 42 (see FIG. 1), a radiation conversion panel 84 for converting radiation 56 that has passed through the subject 42 into electrical charge information, and a lead plate 86 for absorbing back scattered rays of the radiation 56, which are successively arranged in this order from surfaces of the casings 80 that are irradiated with radiation 56. The irradiated surfaces of the casings 80 may be constructed as the grid 82.

The radiation conversion panel 84, which is a so-called flat panel detector (FPD), may be a direct conversion type of radiation detector that senses and directly converts radiation 56 into electrical charges and stores the converted electrical charges, or an indirect conversion type of radiation detector that converts radiation 56 into visible light, converts the thus-converted visible light into electrical charges, and stores the electrical charges. In the following explanation, a case shall be described in which the radiation conversion panel 84 is an indirect type of radiation conversion panel.

The casing 80 also houses therein a battery 88 as a power supply for the radiation conversion panel 84, a controller 90 for energizing the radiation conversion panel 84 with electric power supplied from the battery 88, and a transceiver 92 for sending signals representing a radiographic image of the subject 42, which has been stored in the radiation conversion panel 84, to the consoles 24, 26, 28 via the control apparatus 40 (see FIG. 1). Further, the casing 80 includes a power supply switch 94 on a side wall thereof for activating the radiation detection devices 52, 62, 72.

Figure 3:
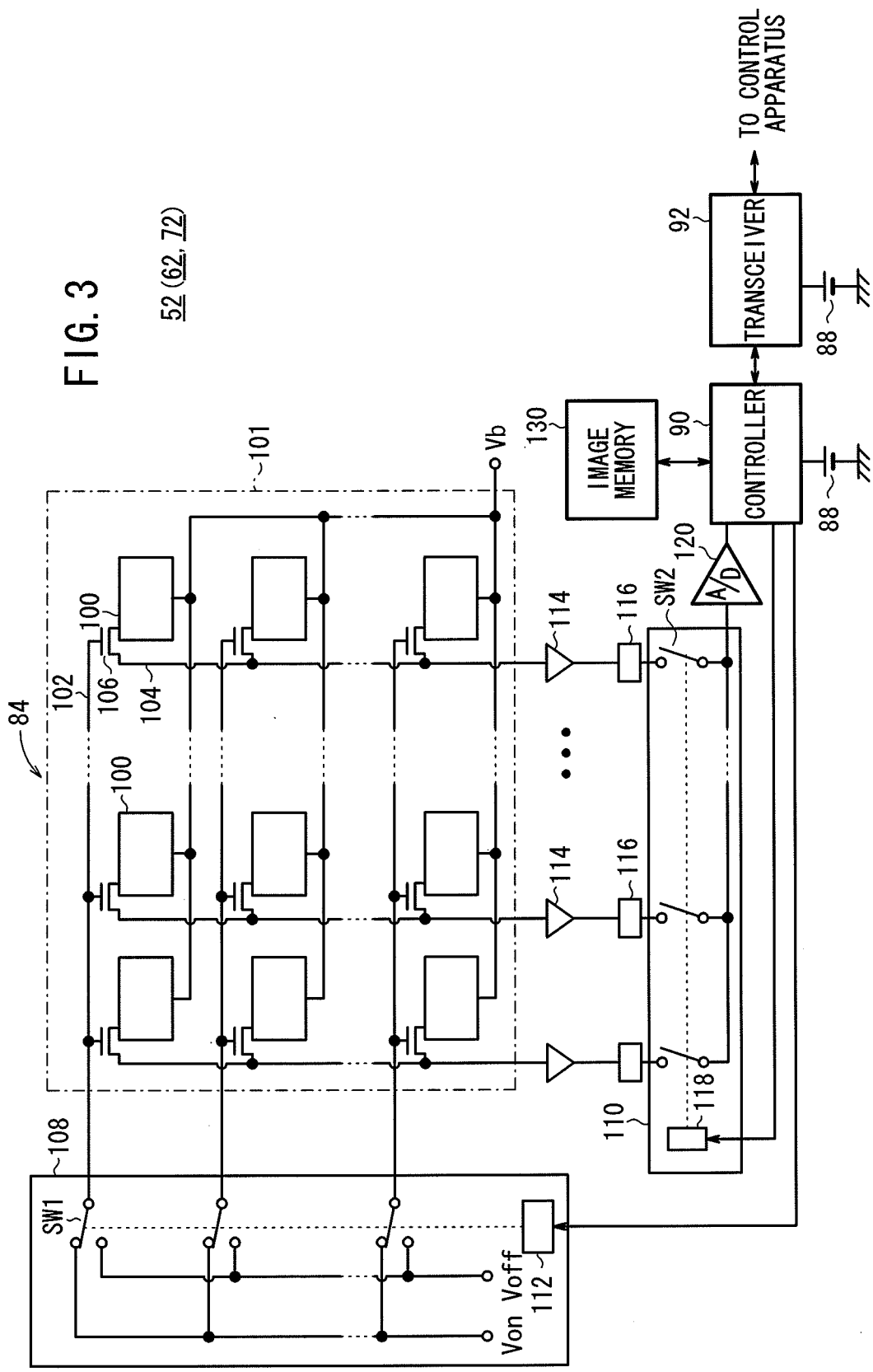
FIG. 3 is a circuit diagram of the radiation detection device of FIG. 2.

Next, an explanation shall be given with reference to FIG. 3 concerning the circuit structure inside the radiation detection devices 52, 62, 72.

The radiation conversion panel 84 comprises an array of thin-film transistors (TFTs) 106 arranged in rows and columns, and a photoelectric conversion layer 101 made up of solid state detection elements 100 (hereinafter also referred to as pixels) made of a material such as amorphous silicon (a-Si) or the like for converting visible light into electrical signals. The photoelectric conversion layer 101 is disposed on the array of TFTs 106. In this case, in each of the pixels 100, which are supplied with a bias voltage Vb from the battery 88, electrical charges, which are generated by conversion of visible light into electrical signals (analog signals), are stored. Then, when the TFTs 106 are turned on one row at a time, the electrical charges can be read from the pixels 100 as image signals.

The TFTs 106 are connected respectively to the pixels 100. Gate lines 102, which extend parallel to the rows, and signal lines 104, which extend parallel to the columns, are connected to the TFTs 106. The gate lines 102 are connected to a line scanning driver 108, and the signal lines 104 are connected to a multiplexer 110. The gate lines 102 are supplied with control signals Von, Voff from the line scanning driver 108 for turning on and off the TFTs 106 along the rows. The line scanning driver 108 comprises a plurality of switches SW1 for switching between the gate lines 102, and an address decoder 112 for outputting a selection signal for selecting one of the switches SW1 at a time. The controller 90 supplies address signals to the address decoder 112.

The signal lines 104 are supplied with electrical charges stored by the pixels 100 through the TFTs 106 arranged in the columns. The electrical charges are amplified by amplifiers 114. The amplifiers 114 are connected through respective sample and hold circuits 116 to the multiplexer 110. The multiplexer 110 comprises a plurality of switches SW2 for successively switching between the signal lines 104, and an address decoder 118 for outputting selection signals for selecting one of the switches SW2 at a time. The address decoder 118 is supplied with address signals from the controller 90. The multiplexer 110 is connected to an A/D converter 120. Radiographic images, which are converted by the A/D converter 120 into digital signals, are supplied to the controller 90. The controller 90 stores the radiographic images made up of digital signals in an image memory 130, or alternatively, sends radiographic images that are stored in the image memory 130 to the control apparatus 40 via the transceiver 92.

The TFTs 106, which function as switching elements, may be combined with another image capturing device, such as a CMOS (Complementary Metal-Oxide Semiconductor) image sensor or the like. Alternatively, the TFTs 106 may be replaced with a CCD (Charge-Coupled Device) image sensor for shifting and transferring electrical charges with shift pulses, which correspond to gate signals in the TFTs.

Figure 4:
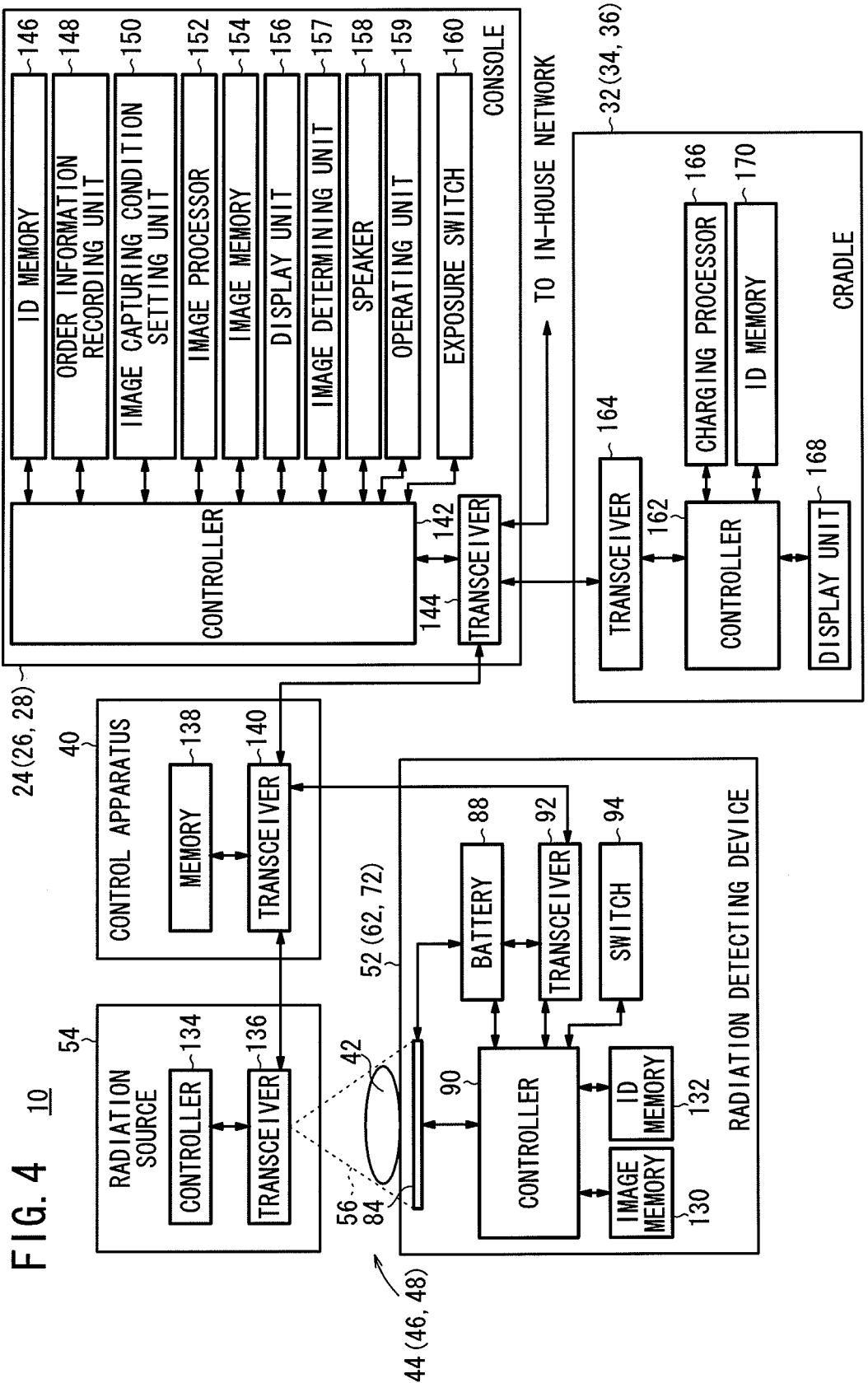
FIG. 4 is a block diagram for explaining in greater detail the radiographic image capturing system of FIG. 1.

FIG. 4 is a block diagram showing in greater detail the radiographic image capturing system 10. Components of the radiographic image capturing system 10, which have not been described above with reference to FIGS. 1 through 3, will primarily be described below with reference to FIG. 4.

The radiation detection devices 52, 62, 72 further include therein ID memories 132, which store ID information for identifying the radiation detection devices 52, 62, 72. Further, the controller 90 carries out calibration processing of the radiation conversion panel 84 (brightness correction, darkness correction and defect correction for a radiographic image) periodically or at times when the radiation detection devices 52, 62, 72 are activated. Respective tables for the brightness correction, darkness correction and defect correction to be carried out by such calibration processing are stored in the image memory 130. Such calibration processing may be performed by application of well known processing methods (see, e.g., Japanese Laid-Open Patent Publication No. 2009-028373).

The radiation source 54 includes a controller 134 for controlling the radiation source 54 in its entirety so as to output radiation 56, and a transceiver 136 for sending and receiving signals between the transceiver 136 and the control apparatus 40.

The control apparatus 40 comprises a memory 138 in which the various tables are stored, and a transceiver 140 for carrying out sending and receiving of signals between transceivers 92 of the radiation detection devices 52, 62, 72, the transceiver 136 of the radiation source 54, and the consoles 24, 26, 28. In this case, the transceiver 140 sends acquired radiographic images to the consoles 24, 26, 28 from image memories 130 of each of the radiation detection devices 52, 62, 72 via the controller 90 and the transceiver 92.

The consoles 24, 26, 28 include, respectively, a controller 142, a transceiver 144, an ID memory (identification information storage unit) 146, an order information memory 148, an image capturing condition setting unit 150, an image processor 152, an image memory 154, a display unit (output device) 156, an image determining unit (image selector) 157, a speaker 158, an operating unit (image selector) 159, and an exposure switch 160.

The transceiver 144 carries out sending and receiving of signals through the in-house network 30 between the HIS 12, the RIS 12, the viewer 16, and other consoles, as well as carrying out sending and receiving of signals between the control apparatus 40 and the cradles 32, 34, 36.

Each of the controllers 142 of the consoles 24, 26, 28 controls in a comprehensive manner the respective components of the consoles 24, 26, 28.

In this case, the controller 142 stores in the order information memory 148 image capturing order information acquired from the RIS 14. Further, the controller 142 stores in the image capturing condition setting unit 150 image capturing conditions for the image capturing apparatus 44, 46, 48, which are acquired from the RIS 14, or are set by a doctor or radiological technician by manipulating the operating unit 159, such as a keyboard, a mouse, or the like.

The order information is information generated by the doctor using the RIS 14. The image capturing order includes patient information including the name, age, gender, etc., for specifying the patient, in addition to an image capturing apparatus to be used for capturing a radiographic image, an image capturing region, an image capturing technique (image capturing method) such as upstanding or recumbent image capturing, and image capturing conditions. The image capturing conditions are conditions for determining a dose of radiation 56 to be applied to the subject 42, e.g., a tube voltage and a tube current of the radiation source 54, an irradiation time of the radiation 56, etc.

In this case, the doctor or radiological technician manipulates the operating unit 159, thereby selecting one of the image capturing apparatus to be used from among the three image capturing apparatus 44, 46, 48 that reside in the image capturing rooms 18, 20, 22, and an image capturing technique for the one image capturing apparatus, together with inputting ID information (identifying information) of the radiation detection device (one of the radiation detection devices) to be used for image capturing. The controller 142 then sets in the image capturing condition setting unit 150 image capturing conditions, including the selected one image capturing apparatus and the image capturing technique, as well as the aforementioned ID information.

Further, the doctor or radiological technician manipulates the operating unit 159 so as to input, in addition to the ID information of the one radiation detection device to be used for image capturing, ID information of all of the radiation detection devices 52, 62, 72 that reside in the image capturing rooms 18, 20, 22 in which image capturing is performed, and ID information of a radiation detection device that is currently being charged by the cradle connected to the one image capturing apparatus. The input ID information is stored in the ID memory 146. Apart from each of the above-mentioned ID information, ID information of all of the radiation detection devices possessed by the hospital may be stored in the ID memory 146. Further, in place of inputting ID information by means of the operating unit 159, bar codes to which the ID information is imparted may be adhered to each of the radiation detection devices, such that the ID information of each of the radiation detection devices may be stored in the ID memory 146 by reading the adhered bar codes using a non-illustrated bar code reader.

Further, when the exposure switch 160 is turned on by the doctor or radiological technician, the controller 142 outputs to the control apparatus 40 the image capturing conditions set in the image capturing condition setting unit 150, and the ID information stored in the ID memory 146 of all of the radiation detection devices 52, 62, 72 inside the one image capturing room.

According to the input image capturing conditions and the ID information, the control apparatus 40, irrespective of whether or not the power supply switch 94 has been turned on, in accordance with activation of the radiation detection devices 52, 62, 72 of each of the image capturing apparatus 44, 46, 48 inside the one image capturing room, causes a bias voltage Vb to be supplied from the batteries 88 thereof to the radiation conversion panels 84, thereby bringing about a condition enabling storage of electrical charges in each of the pixels 100.

Further, the control apparatus 40 controls the radiation source 54 under a condition in which the radiation conversion panels 84 of each of the radiation detection devices 52, 62, 72 are capable of storing electrical charges, thereby causing radiation 56 to be output from the radiation source 54.

Furthermore, after application of radiation 56 with respect to the subject 42 (following image capturing), the control apparatus 40 acquires all of the radiographic images obtained by each of the radiation detection devices 52, 62, 72 inside the one image capturing room, including the radiographic image obtained by the one radiation detection device, and transmits the radiographic images to the consoles 24, 26, 28.

In the event that all of the radiographic images are input from each of the radiation detection devices 52, 62, 72 to the consoles 24, 26, 28 via the control apparatus 40, the image determining unit 157 determines whether or not, among all of the radiographic images, including the radiographic image from the one radiation detection device, there exists a significant radiographic image in which the subject 42 is reflected. The significant radiographic image in which the subject 42 is reflected is defined as a radiographic image in which, for example, in the case that the radiographic image is made up of image data consisting of digital data, an average value or a distributed value of intensity of the image data is equal to or greater than a predetermined threshold. More specifically, in the case of image data, which is displayed in white at a location where the subject 42 is reflected therein as a result of absorption by the subject 42 of a portion of the radiation 56, it is considered that the average value or the distributed value of intensity of the image data is comparatively high. Consequently, image data for which the average value or the distributed value of intensity thereof is equal to or greater than the predetermined threshold is judged by the image determining unit 157 as a significant radiographic image in which the subject 42 is reflected. The average value or the distributed value of intensity may be an average or distributed value of the entire image data, or an average or distributed value of a location in which the subject 42 is reflected.

If the image determining unit 157 judges that a significant radiographic image exists among all of the radiographic images, the image determining unit 157 output the significant radiographic image to the image processor 152, and after image processing thereof, the radiographic image is displayed on the display unit 156.

Further, in the event that the image determining unit 157 judges that a significant radiographic image does not exist, the image determining unit 157 then regards a radiographic image, for which the average value or the distributed value of intensity of the image data thereof is closest to the threshold value (i.e., a radiographic image that enables image reading diagnosis, yet wherein the average value or the distributed value of intensity of the image data is slightly lower than the aforementioned threshold value), as being the significant radiographic image, and outputs the radiographic image, which is regarded as the significant radiographic image, to the image processor 152, and after image processing thereof, the radiographic image can also be displayed on the display unit 156.

Furthermore, with the present embodiment, in place of the image determining unit 157 selecting a significant radiographic image, all of the radiographic images may be displayed on the display unit 156, and a significant radiographic image can be selected by a doctor or radiological technician, or alternatively, even if there is no significant radiographic image, the doctor or radiological technician can select a radiographic image that is capable of enabling image reading diagnosis. In this case, when the doctor or radiological technician manipulates the operating unit 159 and selects, from among all of the radiographic images displayed on the display unit 156, a significant radiographic image or a radiographic image that enables image reading diagnosis, the image processor 152 performs image processing with respect to the selected radiographic image, and after image processing, displays the radiographic image anew on the display unit 156.

Further, in the case that a radiographic image from another radiation detection device, which differs from the radiographic image of the one radiation detection device, is selected by the image determining unit 157, or if a radiographic image from another radiation detection device, which differs from the radiographic image of the one radiation detection device, is selected as a result of the operating unit 159 being manipulated by the doctor or radiological technician, the speaker 158 and/or the display unit 156 can also output a warning (notification) to the doctor or radiological technician, which indicates that a radiographic image from another image capturing apparatus (another radiation detection device) has been selected, which differs from the one image capturing apparatus (the one radiation detection device) that was set in the image capturing conditions.

In the above description, the image determining unit 157 determines whether or not, among the acquired image data, a significant radiographic image (image data) exists in which the subject 42 is reflected based on an average value or a distributed value of intensity of the image data. However, whether or not a significant radiographic image exists in which the subject 42 is reflected may also be determined based on an average value or a distributed value of density of the image data. More specifically, in the case of image data, which is displayed in white at a location where the subject 42 is reflected therein as a result of absorption by the subject 42 of a portion of the radiation 56, it is considered that the average value or the distributed value of density of the image data is comparatively low. Consequently, instead of a determining process based on the average value or the distributed value of intensity, image data for which the average value or the distributed value of density thereof is less than the predetermined threshold is judged by the image determining unit 157 as a significant radiographic image in which the subject 42 is reflected. In this case as well, the average value or the distributed value of density may be an average or distributed value of the entire image data, or an average or distributed value of a location in which the subject 42 is reflected.

Further, the image determining unit 157 may compare the radiographic images from all of the radiation detection devices, so as to determine whether or not there is a significant radiographic image in which the subject 42 is reflected among the radiographic images.

The cradles 32, 34, 36 each include, respectively, a controller 162, a transceiver 164, a charging processor 166, a display unit 168, and an ID memory 170.

Each of the controllers 162 of the cradles 32, 34, 36 carries out comprehensive control of the components housed within the respective cradles 32, 34, 36.

The charging processors 166 perform charging processing with respect to radiation detection devices, which are connected to the cradles 32, 34, 36 outside of the image capturing rooms 18, 20, 22. The transceivers 164 carry out transmission and reception of signals between the transceivers 164 and the transceivers 144 of the consoles 24, 26, 28.

Further, the controller 162 records in the ID memory 170 ID information of the radiation detection device for which charging processing thereon is currently being carried out by the charging processor 166. The display unit 168 displays information (a charge amount, ID information, etc.) of the radiation detection device currently being charged. The controller 162 may also read and record in the ID memory 170 ID information from the ID memory 132 of the radiation detection device, at a time when the cradle and the radiation detection device are connected together. Alternatively, ID information pertaining to the cradle may be acquired and stored in the ID memory 170 from the ID memory 146 of the console that is connected to the cradle.

The radiographic image capturing system 10 according to the present embodiment is constructed basically as described above. Next, an explanation shall be made, in accordance with the flowchart of FIG. 5 and the time chart of FIG. 6, concerning operations (a radiographic image capturing method) centering on the console 24 and the image capturing room 18.

In the following explanations, it shall be assumed that the one radiation detection device and the imaging capturing apparatus inside the image capturing room 18, which are selected by a doctor or radiological technician, are the radiation detection device 72 and the image capturing apparatus 48 for performing upstanding image capturing, whereas the other radiation detection devices and imaging capturing apparatus are the radiation detection device 62 and the image capturing apparatus 46, and the radiation detection device 52 and the image capturing apparatus 44, which are used for recumbent image capturing. Further, during image capturing, a case shall be explained in which the power supply switch 94 is not turned on, but rather wherein each of the radiation detection devices 52, 62, 72 is activated by means of commands from the control apparatus 40.

Figure 5:
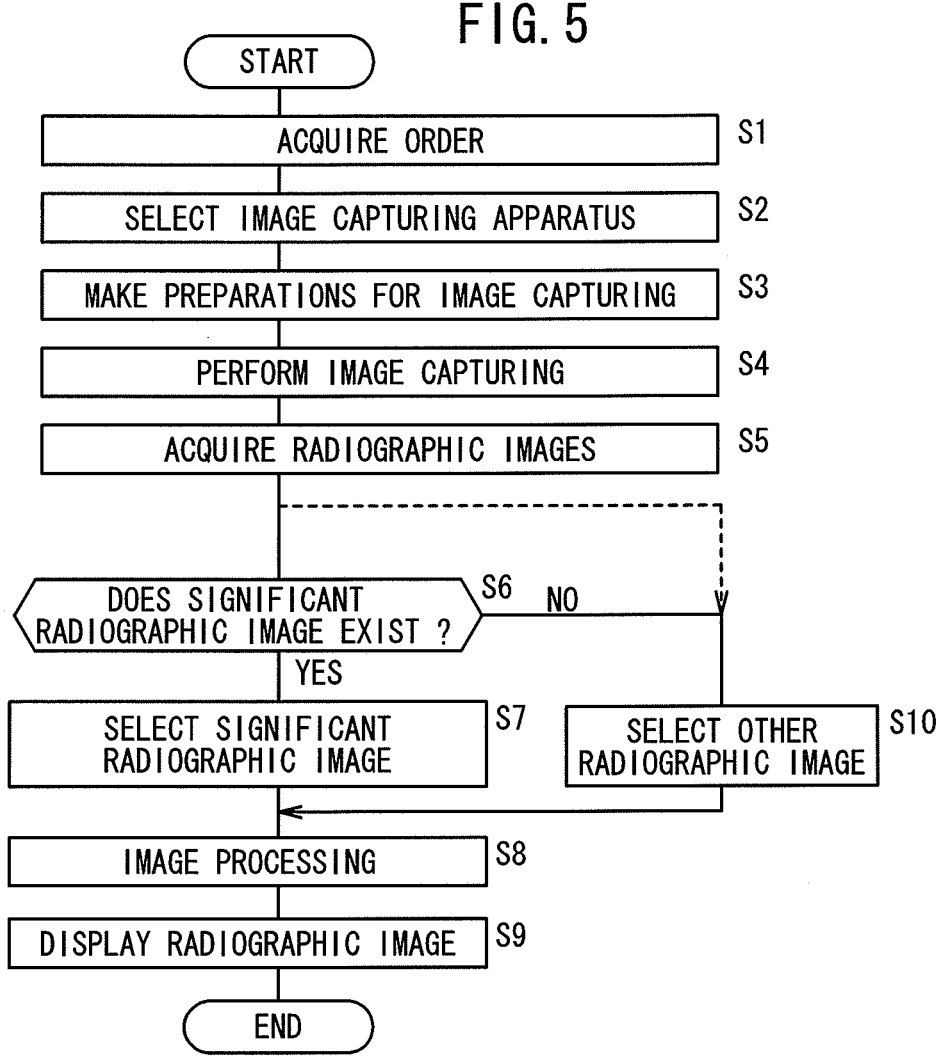
FIG. 5 is a flowchart of an operation sequence of a radiographic image capturing system according to the present embodiment.
Figure 6:
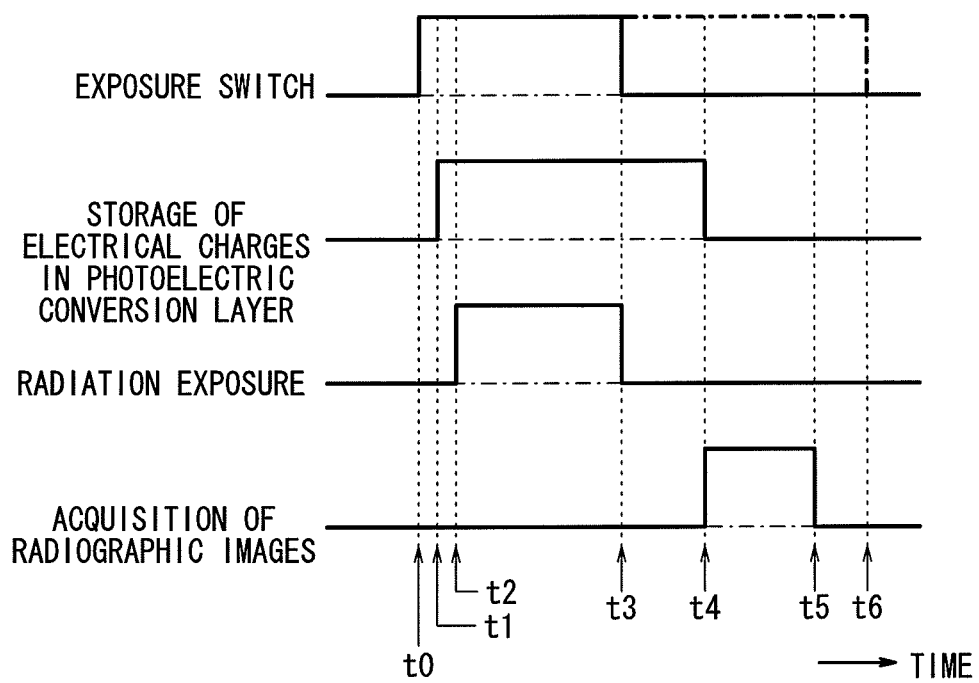
FIG. 6 is a time chart showing passage of time from turning on of a radiation exposure switch until acquisition of a radiographic image is completed.

Furthermore, in the descriptions of FIGS. 5 and 6, a case shall be explained in which, initially, upstanding image capturing with respect to the subject 42 is carried out normally according to the image capturing conditions using the one image capturing apparatus 48. Next, irrespective of the image capturing conditions for upstanding image capturing being set in the image capturing condition setting unit 150, a case shall be explained in which, instead of performing upstanding image capturing using the image capturing apparatus 48, recumbent image capturing is performed using the image capturing apparatus 46.

First, a case shall be explained in which, in accordance with the image capturing conditions, upstanding image capturing is carried out normally with respect to the subject 42, while using the one image capturing apparatus 48 in the image capturing room 18.

In step S1, the transceiver 144 of the console 24 acquires order information from the RIS 14 through the in-house network 30. The acquired order information is stored in the order information memory 148.

In step S2, the doctor or radiological technician manipulates the operating unit 159 of the console 24, thereby causing the order information recorded in the order information memory 148 to be displayed on the display unit 156. Next, while observing the order information displayed on the display unit 156, the doctor or radiological technician manipulates the operating unit 159 and selects the image capturing apparatus 48 to be used for image capturing, as well as the image capturing technique (upstanding image capturing) for the image capturing apparatus 48, together with inputting ID information of the radiation detection device 72. As a result, the selected image capturing apparatus 48 and image capturing technique, the input ID information, and various information among the order information that corresponds to such information are set as image capturing conditions in the image capturing condition setting unit 150. Further, the doctor or radiological technician manipulates the operating unit 159 in order to also input ID information of all of the radiation detection devices 52, 62, 72 that reside in the image capturing room 18, together with ID information of a radiation detection device that currently is being charged by the cradle 32 connected to the console 24. Such ID information is stored in the ID memory 146.

Next, in step S3, the doctor or radiological technician performs preparations for image capturing with respect to the selected image capturing apparatus 48. In this case, after having mounted on the image capturing base 70 a radiation detection device 72, the battery 88 of which has been completely charged by the cradle 32, the doctor or radiological technician positions the subject 42 with respect to the image capturing base 70. Further, the doctor or radiological technician orients the radiation source 54 so as to face toward the subject 42 and the image capturing base 70.

After completion of preparations for image capturing, in step S4, the doctor or radiological technician turns on the exposure switch 160 and starts capturing of an upstanding image with respect to the subject 42.

First, at time t0 in FIG. 6, when the exposure switch 160 is turned on, the controller 142 transmits the image capturing conditions set in the image capturing condition setting unit 150, and the ID information of the radiation detection devices 52, 62, 72 stored in the ID memory 146 to the transceiver 140 of the control apparatus 40 via the transceiver 144. The control apparatus 40 stores the image capturing conditions and the respective ID information received by the transceiver 140 in the memory 138, and controls the radiation source 54 and the radiation detection devices 52, 62, 72 in accordance with the image capturing conditions and the respective ID information, whereupon upstanding image capturing with respect to the subject 42 (i.e., application of radiation 56 with respect to the subject 42) is implemented.

More specifically, at time t1, the control apparatus 40 activates each of the radiation detection devices 52, 62, 72 by means of controls from the controllers 90 via the transceivers 140, 92. In accordance therewith, the controllers 90, following controls from the control apparatus 40, supply bias voltages Vb from the batteries 88 to the radiation conversion panels 84, whereby each of the pixels 100 are brought into a state enabling storage of electrical charges therein. That is, in such a state, the electrical charges can be stored in each of the pixels 100.

At time t2, the control apparatus 40 transmits image capturing conditions to the controller 134 of the radiation source 54 via the transceivers 140, 136, whereupon, based on the received image capturing conditions, the controller 134 causes radiation 56 to be output for a predetermined time period (exposure period) from time t2 until time t3. In accordance therewith, radiation 56 passes through the subject 42 and is applied to the radiation detection device 72 inside the image capturing base 70. Radiation 56 that has passed through the subject 42 is guided to the radiation conversion panel 84, which is disposed inside the radiation detection device 72.

In the case that the radiation detection device 72 is an indirect conversion type of radiation detection device, the scintillator of the radiation conversion panel 84 that constitutes the radiation detection device 72 emits visible light of an intensity corresponding to the intensity of the radiation 56. As noted previously, since from time t1, each of the pixels 100 that make up the photoelectric conversion layer 101 receives the supplied bias voltage Vb, and thus the pixels 100 are in a state enabling storage of electrical charges therein, the aforementioned visible light is converted into electrical signals, which are stored as electrical charges.

In addition, after storage of electrical charges in each of the pixels 100 is completed at time t4, the controller 90, by supplying address signals to the line scanning driver 108 and the multiplexer 110, initiates read out processing of the electrical charge information stored in each of the pixels 100, which makes up the radiographic image of the subject 42.

More specifically, the address decoder 112 of the line scanning driver 108, in accordance with address signals supplied from the controller 90, outputs selection signals for selecting one of the switches SW1 at a time, and supplies control signals Von to gates of the corresponding TFTs 106 that are connected to the gate lines 102. On the other hand, the address decoder 118 of the multiplexer 110, in accordance with address signals supplied from the controller 90, outputs selection signals for switching in succession the switches SW2, whereupon the radiographic image, which is defined by electrical charge information stored in each of the pixels 100 connected to the gate line 102 selected by the line scanning driver 108, is read out successively through the signal lines 104.

Radiographic images, which are read out from the respective pixels 100 connected to the selected gate lines 102, after being amplified by the amplifiers 114, are sampled respectively through the sample and hold circuits 116, supplied to the A/D converter 120 through the multiplexer 110, and are converted into digital signals. Radiographic images, which have been converted into digital signals, are stored through the controller 90 in the image memory 130.

Similarly, the address decoder 112 of the line scanning driver 108 successively switches the switches SW1 according to address signals supplied from the controller 90, whereupon the radiographic image, which is defined by electrical charge information stored in each of the pixels 100 connected to the respective gate lines 102, is read out successively through the signal lines 104, and the radiographic image is stored in the image memory 130 through the multiplexer 110, the A/D converter 120 and the controller 90.

In this manner, a radiographic image, in which the subject 42 in an upstanding condition is reflected, is stored in the image memory 130. In the description of step S4, an explanation has been given concerning the image capturing apparatus 48. However, in the radiation detection devices 52, 62 of the other image capturing apparatus 44, 46 as well, storage of electrical charges and reading out of radiographic images are carried out in the same manner as with the radiation detection device 72. In this case, because radiation 56 is not applied to the radiation detection devices 52, 62, it is a matter of course that the subject 42 is not reflected in the radiographic images of the radiation detection devices 52, 62. Further, in the console 24, during the interval from time t3 to time t6, even if the doctor or radiological technician turns on the exposure switch 160, the function of the exposure switch is disabled (i.e., application of radiation 56 is prohibited). Moreover, time t6 represents a time at which all operations pertaining to one image capturing event shown in the flowchart of FIG. 5 are brought to an end.

In step S5, after image capturing has ended, the control apparatus 40 acquires respectively through the controller 90 and the transceivers 92, 140 the radiographic images stored in the image memories 130, together with the ID information recorded in the ID memories 132 of each of the radiation detection devices 52, 62, 72, and transmits all of the acquired ID information and the radiographic images to the transceiver 144. Accordingly, the transceiver 144 receives the ID information and the radiographic images from each of the radiation detection devices 52, 62, 72, and stores the same in the image memory 154.

In step S6, the image determining unit 157 determines whether or not a significant radiographic image in which the subject 42 is reflected exists among all of the radiographic images that are stored in the image memory 154.

As noted previously, because image capturing is carried out with respect to a subject 42 who is in an upstanding condition in the image capturing apparatus 48, and the subject 42 is reflected in the radiographic image of the radiation detection device 72, the average value or the distributed value of intensity of the radiographic image (image data) is equal to or greater than the predetermined threshold. Consequently, among each of the radiographic images that are stored in the image memory 154, from the fact that the average value or the distributed value of intensity of the radiographic image is equal to or greater than the predetermined threshold, the image determining unit 157 judges that the radiographic image of the radiation detection device 72 is a significant radiographic image (step S6: YES).

Further, because the subject 42 is not reflected in the radiographic images of the other radiation detection devices 52, 62 that are stored in the image memory 154, the average value or the distributed value of intensity of the image data therefrom is less than the threshold. Consequently, the image determining unit 157 judges that the radiographic images of each of the radiation detection devices 52, 62 stored in the image memory 154 are unnecessary.

In addition, the image determining unit 157 selects as the significant radiographic image the radiographic image of the radiation detection device 72 (step S7), and supplies the ID information of the radiation detection device 72 and the radiographic image (i.e., the significant radiographic image) stored in the image memory 154 to the image processor 152, whereas the ID information and the radiographic images of the radiation detection devices 52, 62 stored in the image memory 154 are erased.

The image processor 152 implements prescribed image processing with respect to the supplied radiographic image of the radiation detection device 72 (step S8), and after completion of image processing, displays the radiographic image on the display unit 156 (step S9).

In this manner, during the time period from time t4 until time t5, acquisition processing of radiographic images from the radiation detection devices 52, 62, 72 is completed. The radiographic image displayed on the display unit 156 is transmitted through the in-house network 30 to the viewer 16 to be used by a doctor for performing image reading diagnosis.

An explanation has been given above concerning a case in which upstanding image capturing is performed normally with respect to the subject 42 in the image capturing apparatus 48.

Next, a case shall be described in which, notwithstanding the fact that the image capturing apparatus 48 has been selected by the doctor or radiological technician, and image capturing conditions pertaining to the image capturing apparatus 48 are set in the image capturing condition setting unit 150, upstanding image capturing is not performed by the image capturing apparatus 48, but rather, recumbent image capturing is performed instead using the image capturing apparatus 46.

In this case, according to the image capturing conditions, the doctor or radiological technician had intended to implement upstanding image capturing using the image capturing apparatus 48. However, for example, because of malfunctioning of the image capturing apparatus 48 or the radiation detection device 72, in place of upstanding image capturing by the image capturing apparatus 48, a case shall be assumed in which it was determined to carry out recumbent image capturing using the image capturing apparatus 46. Further, normally, when the image capturing technique is changed, the doctor or radiological technician should manipulate the operating unit 159 in order to change the image capturing conditions registered in the image capturing condition setting unit 150. However, in this case, an explanation shall be made in which the doctor or radiological technician forgets to change such settings, yet recumbent image capturing is carried out anyway using the image capturing apparatus 46.

In step S3, the radiation detection device 62, the battery 88 of which has been charged by the cradle 32, is mounted on the image capturing base 60. Next, the doctor or radiological technician positions the subject 42 with respect to the image capturing base 60, and orients the radiation source 54 so as to face toward the subject 42 and the image capturing base 60.

In step S4, after preparations for image capturing have been completed, the doctor or radiological technician turns on the exposure switch 160 and initiates recumbent image capturing with respect to the subject 42.

In this case, the image capturing apparatus 48, which is indicated by the image capturing conditions set in the image capturing condition setting unit 150, differs from the image capturing apparatus 46 actually used to perform image capturing. Moreover, even if the doctor or radiological technician is aware that a recumbent image is being captured using the image capturing apparatus 46, because a setting change of the image capturing conditions has not been carried out, the console 24 mistakenly recognizes that image capturing is performed based on the image capturing conditions (upstanding image capturing), which currently are set in the image capturing condition setting unit 150.

Thus, when the exposure switch 160 is turned on at time to in FIG. 6, the image capturing conditions and the ID information of the radiation detection devices 52, 62, 72 stored in the ID memory 146 are sent from the console 24 to the control apparatus 40, and the control apparatus 40 records the received image capturing conditions and the respective ID information in the memory 138. Together therewith, the control apparatus 40 controls the radiation source 54 and each of the radiation detection devices 52, 62, 72 according to the image capturing conditions and the ID information. Based on the image capturing conditions and the ID information, the control apparatus 40 controls the radiation source 54 and each of the radiation detection devices 52, 62, 72 under a condition in which it is recognized that upstanding image capturing is being carried out.

At time t1, the control apparatus 40 activates each of the radiation detection devices 52, 62, 72, whereby each of the pixels 100 are brought into a state enabling storage of electrical charges therein. At time t2, image capturing conditions are sent to the radiation source 54. In accordance therewith, during the exposure period from time t2 until time t3, radiation 56 is applied to the subject 42, and radiation that has passed through the subject 42 is guided to the radiation conversion panel 84 inside the radiation detection device 62. The scintillator of the radiation conversion panel 84 emits visible light of an intensity that corresponds to the intensity of the radiation 56, whereupon in each of the pixels 100, the visible light is converted into electrical signals, which are stored as electrical charges.

Furthermore, at time t4 after storage of electrical charges in the pixels 100 is completed, the controller 90, by supplying address signals to the line scanning driver 108 and the multiplexer 110, initiates a process to read out the electrical charge information, which defines a radiographic image of the subject 42 stored in the respective pixels 100, and the read out radiographic image is stored in the image memory 130.

In this case, a radiographic image, in which the subject 42 in a recumbent state is reflected, is stored in the image memory 130 of the radiation detection device 62. Consequently, it also follows that the subject 42 is not reflected either in the radiographic image of the radiation detection device 72, which was selected by the doctor or radiological technician, or in the radiographic image of the other radiation detection device 52.

In step S5, the control apparatus 40 acquires the ID information and the radiographic images from each of the radiation detection devices 52, 62, 72, and transmits the same to the transceiver 144.

In step S6, the image determining unit 157 determines whether or not a significant radiographic image in which the subject 42 is reflected exists among the three radiographic images that are stored in the image memory 154.

As noted previously, because image capturing is carried out with respect to a subject 42 who is in a recumbent condition in the image capturing apparatus 46, the subject 42 is reflected in the radiographic image of the radiation detection device 62, and consequently, the average value or the distributed value of intensity of the radiographic image (image data) is equal to or greater than the predetermined threshold. On the other hand, because the subject is not reflected in the radiographic images of the radiation detection devices 52, 72, the average value or the distributed value of intensity of the image data therefrom is less than the threshold. Accordingly, the image determining unit 157 determines that a significant radiographic image exists (step S6: YES), and selects as the significant radiographic image the radiographic image of the radiation detection device 62 (step S7).

As a result thereof, the image determining unit 157 supplies the ID information and the radiographic image (the significant radiographic image) of the radiation detection device 62 recorded in the image memory 154 to the image processor 152, whereas the ID information and the radiographic images of the radiation detection devices 52, 72 recorded in the image memory 154 are erased.

The image processor 152 implements prescribed image processing with respect to the supplied radiographic image of the radiation detection device 62 (step S8), and after completion of image processing, displays the radiographic image on the display unit 156 (step S9).

Because the image determining unit 157 has selected as the significant radiographic image the radiographic image of another radiation detection device 62, which differs from the radiation detection device 72 indicated in the image capturing conditions set in the image capturing condition setting unit 150, an audible warning may be output through the speaker 158 and/or a warning may be displayed on the display unit 156, in order to notify the doctor or radiological technician that the radiographic image (the upstanding radiographic image by the image capturing apparatus 48) that corresponds to the image capturing conditions, and the radiographic image actually obtained (the recumbent radiographic image by the image capturing apparatus 46) are not in agreement with each other.

An explanation has been given above concerning a case in which recumbent image capturing is performed by the image capturing apparatus 46, in place of upstanding image capturing performed by the image capturing apparatus 48.

In the case that the recumbent image is captured by the image capturing apparatus 44 and not by the image capturing apparatus 46, it is a matter of course that, according to the above-described method, the radiographic image of the radiation detection device 52 of the image capturing apparatus 44 is selected as the significant radiographic image.

Further, in step S6, in the case that the average value or the distributed value of intensity of all of the image date is less than the threshold (step S6: NO), then although all of the radiographic images are regarded as insignificant, the image determining unit 157 selects from among all of the radiographic images a radiographic image which is capable of enabling image reading diagnosis and for which the average value or the distributed value of intensity is closest to the threshold (step S10). The processes from step S8 and subsequent steps are then carried out with respect to the selected radiographic image.

Furthermore, in place of the radiographic image being automatically selected by the image determining unit 157 as mentioned above, in the case that a significant radiographic image or a radiographic image that enables image reading diagnosis is selected by a doctor or radiological technician, in step S10 following step S5, all of the radiographic images are displayed on the display unit 156, and from among all of the radiographic images, a significant radiographic image or a radiographic image that enables image reading diagnosis may be selected by the doctor or radiological technician through manipulation of the operating unit 159. In accordance therewith, the image processor 152 carries out the process of step S8 with respect to the selected radiographic image, and following image processing, the radiographic image is displayed anew on the display unit 156 (step S9).

As described above, according to the present embodiment, the control apparatus 40 acquires all of the radiographic images from the plurality of radiation detection devices 52, 62, 72, including the radiographic image from the one radiation detection device.

As a result thereof, even in the case that radiation 56 was applied through the subject 42 to the one radiation detection device, or if another radiation detection device is used and radiation 56 was applied through the subject 42 to the other radiation detection device, since the control apparatus 40 acquires radiographic images from all of the radiation detection devices 52, 62, 72, among all of the acquired radiographic images, the subject 42 will necessarily be reflected in one of the radiographic images.

Consequently, according to the present embodiment, since a radiographic image in which the subject 42 is reflected can be acquired reliably and with certainty, unnecessary exposure to radiation with respect to the subject 42 can be prevented.

Further, the image determining unit 157 judges the one radiographic image, from among each of the radiographic images acquired by the control apparatus 40, as the significant radiographic image in which the subject 42 is reflected. As a result thereof, among all of the radiographic images acquired by the control apparatus 40, it is possible to specify which of the radiographic images is the significant radiographic image in which the subject 42 is reflected.

Further, in the case that the image determining unit 157 determines that a significant radiographic image does not exist, because any one of the radiographic images is selected to be regarded as the significant radiographic image, even if a significant radiographic image cannot be obtained, a situation in which a radiographic image of the subject 42 must be recaptured can be avoided by regarding as the significant radiographic image a radiographic image capable of enabling image reading diagnosis yet wherein, for example, the average value or the distributed value of intensity of the image data is slightly lower than the threshold value.

Further, all of the radiographic images may be displayed on the display unit 156, and from among each of the radiographic images, a doctor or radiological technician may manipulate the operating unit 159 and select any one of the radiographic images to be regarded as a significant radiographic image in which the subject 42 is reflected. In this case, although determination of the significant radiographic image is not carried out automatically by the image determining unit 157, by letting the doctor or radiological technician select the significant radiographic image, a radiographic image capable of enabling image reading diagnosis can be obtained.

Further, because with the consoles 24, 26, 28, the significant radiographic image is displayed on the display unit 156, a doctor is capable of performing an image reading diagnosis using the significant radiographic image.

Further, because ID information of all of the radiation detection devices 52, 62, 72 that reside in the image capturing rooms 18, 20, 22 are stored in the ID memories 146, the control apparatus 40 records in the memory 138 thereof respective ID information from the ID memories 146, and in accordance with each of such ID information and the image capturing conditions, all of the radiographic images of each of the radiation detection devices 52, 62, 72 residing in the image capturing rooms 18, 20, 22 are acquired.

Owing thereto, because acquisition processing of radiographic images is carried out only with respect to each of the radiation detection devices 52, 62, 72 that reside in the image capturing rooms 18, 20, 22, mistakenly carrying out of acquisition processing with respect to radiation detection devices outside of the image capturing rooms 18, 20, 22 (for example, radiation detection devices currently being charged by the cradles 32, 34, 36, or radiation detection devices of other image capturing rooms in which image capturing is not being performed) can securely be prevented, and acquisition processing of the radiographic images can be performed highly efficiently.

Furthermore, because each of the radiation conversion panels 84 is placed in a state enabling storage of electrical charges before radiation 56 is applied with respect to the subject 42, it is unnecessary to apply radiation 56, as a trigger for instructing each of the radiation conversion panels 84 to store electrical charges, to each of the radiation detection devices 52, 62, 72 before actual image capturing is performed, whereby the structure for instructing storage of electrical charges can be simplified, and the radiation exposure amount to the subject 42 can be lessened.

In the foregoing description, the control apparatus 40 is provided separately from the consoles 24, 26, 28. However, the radiographic image acquisition functions in the control apparatus 40 may be possessed and carried out by the controllers 142, thereby enabling the control apparatus 40 to be eliminated.

Further, when a radiographic image is captured of a subject 42 that is comparatively thick, a possibility exists for a radiation dose amount, which is leaked to other radiation detection devices, to become greater than the irradiation dose of radiation 56 that reaches the radiation detection device used for image capturing. For this purpose, in the present embodiment, correlation data between an mAs value and the thickness of the subject 42, or a radiographic image pattern during leakage, may be recorded beforehand in the image capturing condition setting unit 150, so that when a radiographic image of a comparatively thick subject 42 is acquired, the radiographic image may be corrected using the recorded data or pattern.

Further, in the foregoing description, a case was explained in which a doctor or radiological technician records an image capturing technique in the image capturing condition setting unit 150 by manipulating the operating unit 159, and when preparations for image capturing are performed, the doctor or radiological technician orients the radiation source 54 to face toward the subject 42. However, the present embodiment is not limited to this feature. For example, in the case that an association is established between the image capturing technique and movement of the radiation source 54, and the image capturing technique is recorded in the image capturing condition setting unit 150, the radiation source 54 may be moved automatically according to the image capturing conditions. Alternatively, when the radiation source 54 is moved when performing preparations for image capturing, the image capturing technique may be recorded automatically in the image capturing condition setting unit 150 responsive to how the radiation source 54 has been moved.

Furthermore, for example, in the event that the image capturing technique is changed from the image capturing apparatus 48 to the image capturing apparatus 46, following the change thereof, the radiation dose in the image capturing conditions may also be changed corresponding to the changed image capturing technique, and radiation 56, the radiation dose of which has been changed, may be output from the radiation source 54.

Although a certain preferred embodiment of the present invention has been shown and described in detail, it should be understood that various changes and modifications may be made to the embodiment without departing from the scope of the invention as set forth in the appended claims.

What is claimed is:

1. A radiographic image acquiring apparatus in which, in the event that one radiation detection device is selected from among a plurality of radiation detection devices, each of which is capable of converting radiation into a radiographic image, the radiographic image acquiring apparatus comprises:
   an acquisition unit for acquiring all of the radiographic images from the plurality of radiation detection devices, including the radiographic image from the one radiation detection device, at a time when application of radiation with respect to a subject is carried out; and
   a determining unit for determining, from among each of the radiographic images acquired by the acquisition unit, a significant radiographic image in which the subject is reflected.

2. The radiographic image acquiring apparatus according to claim 1, further comprising an image selector which, in the case that the determining unit determines that the significant radiographic image does not exist, selects from among each of the radiographic images, any one of the radiographic images to be regarded as the significant radiographic image.

3. A radiographic image acquiring apparatus in which, in the event that one radiation detection device is selected from among a plurality of radiation detection devices, each of which is capable of converting radiation into a radiographic image, the radiographic image acquiring apparatus comprises:
   an acquisition unit for acquiring all of the radiographic images from the plurality of radiation detection devices, including the radiographic image from the one radiation detection device, at a time when application of radiation with respect to a subject is carried out; and
   an image selector for selecting, from among each of the radiographic images acquired by the acquisition unit, any one of the radiographic images to be regarded as a significant radiographic image in which the subject is reflected.

4. The radiographic image acquiring apparatus according to claim 1, further comprising an output device for outputting to the exterior the significant radiographic image.

5. The radiographic image acquiring apparatus according to claim 1, further comprising an identification information storage unit which, in the event that application of radiation with respect to the subject is carried out in an image capturing room, stores identifying information of the plurality of radiation detection devices that reside in the image capturing room,
   wherein based on the identifying information stored in the identification information storage unit, the acquisition unit acquires all of the radiographic images from the plurality of radiation detection devices that reside in the image capturing room.

6. The radiographic image acquiring apparatus according to claim 1, wherein the plurality of radiation detection devices each comprise, respectively, a radiation conversion panel, which converts the radiation into electrical charges and stores the electrical charges, and outputs the stored electrical charges to the exterior as electrical signals, each of the radiation conversion panels obtaining a state enabling storage of the electrical charges before the radiation is applied with respect to the subject.

7. A radiographic image capturing method, comprising the steps of:

in the event that one radiation detection device is selected from among a plurality of radiation detection devices, each of which are capable of converting radiation into a radiographic image, carrying out application of the radiation with respect to a subject;

acquiring, by an acquisition unit, all of the radiographic images from the plurality of radiation detection devices, including the radiographic image from the one radiation detection device, and determining, by a determining unit, a significant radiographic image, in which the subject is reflected, from among each of the radiographic images acquired by the acquisition unit.

8. The radiographic image capturing method according to claim 7, further comprising the step of:

storing, in an identification information storage unit, identifying information of the plurality of radiation detection devices that reside in the image capturing room, in the event that application of radiation with respect to the subject is carried out in an image capturing room, wherein in the step of acquiring all the radiographic images, the acquisition unit acquires all of the radiographic images from the plurality of radiation detection devices that reside in the image capturing room, based on the identifying information stored in the identification information storage unit.

9. The radiographic image acquiring apparatus according to claim 3, further comprising an output device for outputting to the exterior the significant radiographic image.

10. The radiographic image acquiring apparatus according to claim 3, further comprising an identification information storage unit which, in the event that application of radiation with respect to the subject is carried out in an image capturing room, stores identifying information of the plurality of radiation detection devices that reside in the image capturing room, wherein based on the identifying information stored in the identification information storage unit, the acquisition unit acquires all of the radiographic images from the plurality of radiation detection devices that reside in the image capturing room.

11. The radiographic image acquiring apparatus according to claim 3, wherein the plurality of radiation detection devices each comprise, respectively, a radiation conversion panel, which converts the radiation into electrical charges and stores the electrical charges, and outputs the stored electrical charges to the exterior as electrical signals, each of the radiation conversion panels obtaining a state enabling storage of the electrical charges before the radiation is applied with respect to the subject.

* * * * *